United States Patent
Toliver et al.

(10) Patent No.: US 11,760,867 B2
(45) Date of Patent: Sep. 19, 2023

(54) POLYMER COMPOSITIONS AND ARTICLES COATED THEREWITH

(71) Applicant: Church & Dwight Co., Inc., Princeton, NJ (US)

(72) Inventors: Jon Toliver, Franklin Park, NJ (US); Rajesh Ranjan, Princeton, NJ (US); Muthiah Thiyagarajan, Flemington, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 137 days.

(21) Appl. No.: 17/125,357

(22) Filed: Dec. 17, 2020

(65) Prior Publication Data

US 2021/0189103 A1 Jun. 24, 2021

Related U.S. Application Data

(60) Provisional application No. 62/952,601, filed on Dec. 23, 2019.

(51) Int. Cl.
| | |
|---|---|
| *C08L 7/02* | (2006.01) |
| *A61F 6/04* | (2006.01) |
| *C08K 5/00* | (2006.01) |
| *C08L 71/02* | (2006.01) |

(52) U.S. Cl.
CPC ............... *C08L 7/02* (2013.01); *A61F 6/04* (2013.01); *C08K 5/0025* (2013.01); *C08L 71/02* (2013.01)

(58) Field of Classification Search
CPC ... C08L 7/02; C08L 71/02; A61F 6/04; C08K 5/0025
USPC .................................................... 524/575.5
See application file for complete search history.

(56) References Cited

U.S. PATENT DOCUMENTS

| | | |
|---|---|---|
| 6,353,148 B1 | 3/2002 | Gross |
| 6,772,443 B2 | 8/2004 | Soerens et al. |
| 8,110,266 B2 | 2/2012 | Chen et al. |
| 8,137,735 B2 | 3/2012 | Wang et al. |
| 8,512,795 B2 | 8/2013 | Dias et al. |
| 8,871,869 B2 | 10/2014 | Dias et al. |
| 8,932,662 B2 * | 1/2015 | Nielsen ............ A61L 29/085 528/425 |
| 9,080,025 B2 | 7/2015 | Chen et al. |
| 9,085,663 B2 | 7/2015 | Chen et al. |
| 9,579,426 B2 | 2/2017 | Chen et al. |
| 10,449,084 B2 | 10/2019 | Chin et al. |
| 2002/0018898 A1 | 2/2002 | Opolski |
| 2006/0141186 A1 | 6/2006 | Janssen et al. |
| 2008/0227913 A1 | 9/2008 | Koide |
| 2012/0003430 A1 * | 1/2012 | Ceulemans ........... C09J 133/14 156/332 |
| 2017/0107403 A1 * | 4/2017 | Woo .................... C09D 107/02 |
| 2017/0130019 A1 | 5/2017 | Sun et al. |
| 2017/0157298 A1 | 6/2017 | Diemeer et al. |
| 2019/0060530 A1 | 2/2019 | Choudhury et al. |
| 2019/0125934 A1 | 5/2019 | Zhao et al. |
| 2019/0167468 A1 | 6/2019 | Chin et al. |

FOREIGN PATENT DOCUMENTS

| | | |
|---|---|---|
| EP | 0690077 | 1/1996 |
| EP | 1667747 | 6/2006 |
| EP | 1865922 | 10/2009 |
| WO | 1999019006 | 4/1999 |
| WO | 2005060856 | 7/2005 |
| WO | 2017007430 | 1/2017 |
| WO | WO 2019/046906 | 3/2019 |

* cited by examiner

*Primary Examiner* — Hui H Chin

(74) *Attorney, Agent, or Firm* — Church & Dwight Co., Inc.

(57) ABSTRACT

The present disclosure provides compositions and products formed therefrom. In particular, the disclosure provides polymer compositions and hydrogel-latex compositions in particular. Such compositions can include a water-soluble polymer, a natural or synthetic rubber latex, and a rheological stabilizer. The present disclosure further provides products and articles that include a coating layer of the polymer composition on at least a portion of a surface thereof. The coating formed of the polymer composition can impart improved properties to the product or article, such as improved moisture absorption, improved lubricity, and the like.

27 Claims, 3 Drawing Sheets

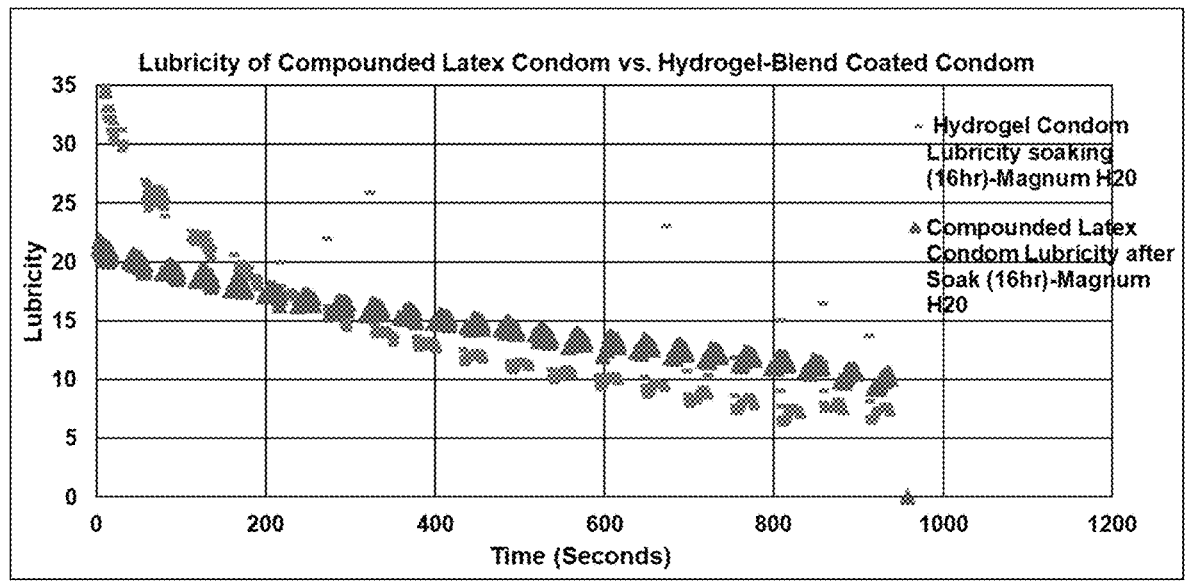
FIG. 3
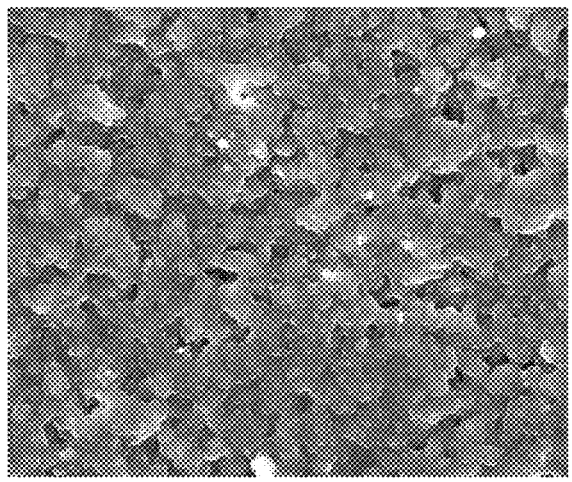 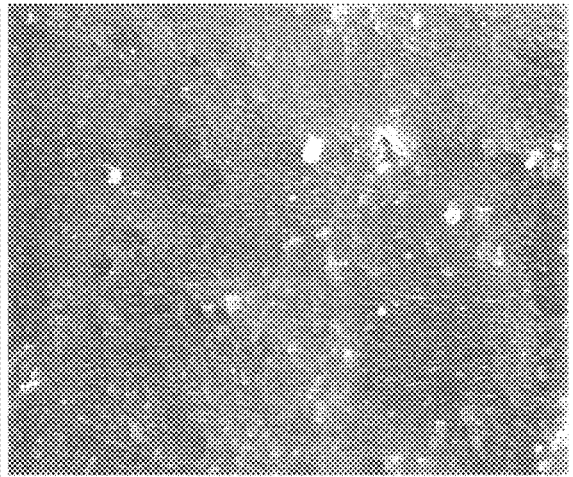
FIG. 4A        FIG. 4B

POLYMER COMPOSITIONS AND ARTICLES COATED THEREWITH

CROSS-REFERENCE TO RELATED APPLICATIONS

The present application claims priority to U.S. Provisional Pat. App. No. 62/952,601, filed Dec. 23, 2019, the disclosure of which is incorporated herein by reference in its entirety.

FIELD OF THE DISCLOSURE

The present disclosure relates to polymer compositions and articles that are coated with the polymer compositions, such as elastomeric articles, and particularly thin-walled products, such as condoms. The polymer compositions in particular may be adapted to or configured to form a hydrogel in the presence of an aqueous fluid and thus provide lubricity to an article coated with the polymer composition.

BACKGROUND

Natural rubber latex and synthetic latex materials are well known for use in forming thin-walled, elastomeric article, such as gloves and condoms. Such materials, however, typically exhibit poor properties in relation to lubricity. For example, natural and synthetic latex polymer articles are typically hydrophobic and do not absorb or retain moisture to any significant degree. Likewise, even when coated with lubricating material, natural and synthetic latex polymer articles can exhibit undesirably high frictional forces such that repeated skin contact can lead to discomfort, pain, and even tissue damage.

SUMMARY OF THE DISCLOSURE

The present disclosure provides compositions of polymeric materials and articles including a coating thereon of the polymeric material. The polymeric material used for the coating may comprise a water-soluble polymer and a latex component, and the water-soluble polymer and latex polymer may combine (as a combination of the two components or as a combination the two components with one or more additives) to form a hydrogel-latex composition.

In one or more embodiments, the present disclosure thus can relate to hydrogel-latex compositions. Such compositions can comprise a water-soluble polymer, a natural or synthetic rubber latex polymer, and a rheological stabilizer. Preferably, the water-soluble polymer and the natural or synthetic rubber latex polymer can be present in a sufficient amount such that the hydrogel-latex composition has a total solids content of about 2.0% to about 20%. In further embodiments, the hydrogel-latex compositions may be defined in relation to one or more of the following statements, which may be combined in any number and order.

The water-soluble polymer can be configured to form an interpenetrating polymer network.

The water-soluble polymer can have a molecular weight of about 1,000,000 Da to about 6,000,000 Da.

The water-soluble polymer can be a polyethylene oxide.

The natural or synthetic rubber latex can be compounded with one or both of a crosslinking agent and a cure accelerator.

The natural or synthetic rubber latex can be at least partially pre-vulcanized.

The rheological stabilizer can be a hydrophobically modified alkali swellable emulsion ("HASE") polymer.

The water-soluble polymer can be present as an aqueous solution in an amount of under 50% by weight based on the total weight of the hydrogel-latex composition.

The water-soluble polymer can be present as an aqueous solution in an amount of about 15% to about 48% by weight based on the total weight of the hydrogel-latex composition.

The natural or synthetic rubber latex can be present as an aqueous dispersion in an amount of less than 30% by weight based on the total weight of the hydrogel-latex composition.

The natural or synthetic rubber latex can be present as an aqueous dispersion in an amount of about 10% to about 30% by weight based on the total weight of the hydrogel-latex composition.

The rheological stabilizer can be present in an amount of less than 1% by weight based on the total weight of the hydrogel-latex composition.

The rheological stabilizer can be present in an amount of about 0.01% to about 0.25% by weight based on the total weight of the hydrogel-latex composition.

The water-soluble polymer can be a homopolymer.

The water-soluble polymer can be substantially non-crosslinked.

The hydrogel-latex composition can comprise: about 20% to about 48% by weight of an aqueous solution of the water-soluble polymer; about 15% to about 30% by weight of an aqueous dispersion of the natural or synthetic rubber latex; about 0.01% to about 0.5% by weight of the rheological stabilizer; and balance water; wherein the foregoing amounts are based on the total weight of the hydrogel-latex composition.

In some embodiments, the present disclosure may provide products or articles of manufacture. Such products/articles can comprise an elastomeric latex with at least a portion of the elastomeric latex being coated with the hydrogel-latex composition as otherwise described herein.

In one or more embodiments, the present disclosure further can provide elastomeric articles in particular. For example, such elastomeric articles can comprise a layer of a latex composition, and a layer of a hydrogel-latex composition as otherwise described herein present on at least a portion of the layer of the latex composition. In further embodiments, such articles may be further defined in relation to one or more of the following statements, which can be combined in any number and order.

The layer of the latex composition can define a condom.

The layer of the latex composition can comprise a natural rubber latex.

The layer of the latex composition can comprise a synthetic polymer latex.

A layer of the latex composition that does not have a layer of the hydrogel-latex composition present thereon can exhibit a first contact angle, and wherein the layer of the hydrogel-latex composition present on at least a portion of the layer of the latex composition can exhibit a second contact angle that is less than the first contact angle.

The second contact angle can be less than the first contact angle by at least 5 degrees.

The layer of the hydrogel-latex composition can have a thickness of about 10 μm to about 100 μm.

BRIEF DESCRIPTION OF THE FIGURES

FIG. 3 is a graph showing lubricity after soaking for 16 hours of a compounded latex condom versus a latex condom coated with a hydrogel-blend composition according to embodiments of the present disclosure.

FIG. 4A is a scanning electron microscope (SEM) image of a surface of a hydrogel-blend coating layer according to embodiments of the present disclosure on a latex condom.

FIG. 4B is an SEM image of a surface of a compounded latex condom with no coating thereon.

DETAILED DESCRIPTION OF THE DISCLOSURE

Figure 1:
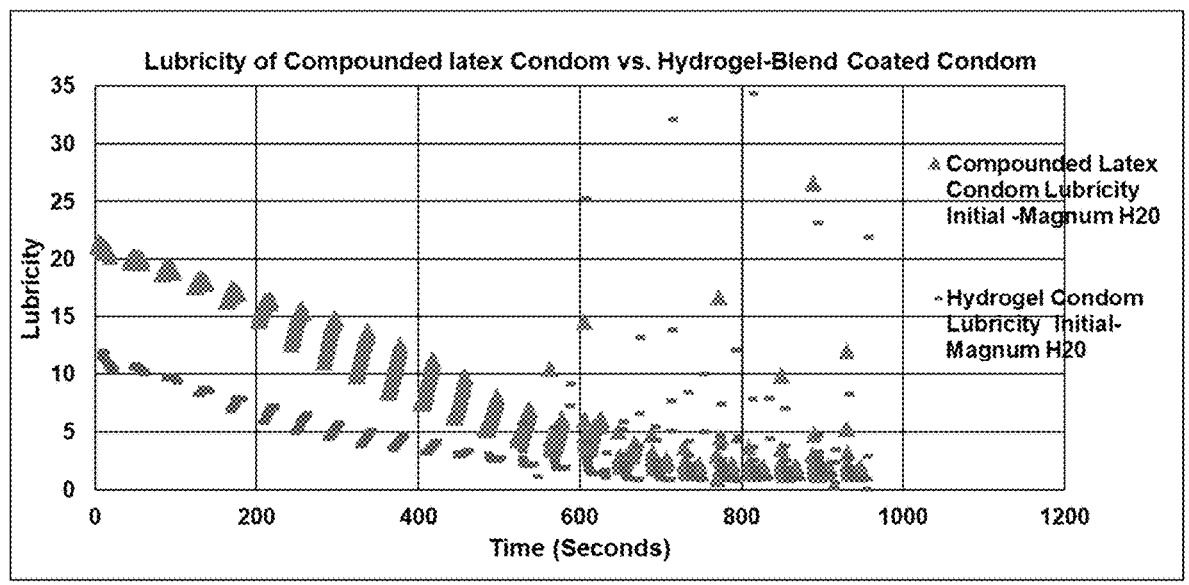
FIG. 1 is a graph showing lubricity of a compounded latex condom versus a latex condom coated with a hydrogel-blend composition according to embodiments of the present disclosure.

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to polymer compositions and articles that are at least partially coated with the polymer compositions. The polymer compositions include hydrogel-forming components, are water-based, and can be applied to a wide variety of substrates to provide a coating layer thereon and impart desired properties. Further, the polymer compositions can be adapted or configured to be applied to a substrate without the requirement of additional solvents and/or without the requirement of acid or other chemical surface priming steps. As such, the polymer compositions can provide stable and durable coatings on articles that have substantially constant dimensions as well as elastomeric articles having significant stretch and/or relaxation properties. Articles having the polymer composition applied thereto as a coating layer can provide increased moisture adsorption and subsequent absorption of moisture into the coating layer, and this can be beneficial to provide lubricity to the coated article. As such, the polymer composition is particularly useful for providing coating layers on articles, such as condoms or elastomeric articles used as barriers in medical fields.

In one or more embodiments, the present disclosure can provide polymer compositions that minimally include both of a hydrogel-forming component and a latex polymer component. As such, the polymer compositions may be characterized as a hydrogel-latex composition in that the hydrogel-forming component and the latex polymer component are blended and can provide a substantially uniform polymer composition of the two base components. Further components may be utilized in the polymer composition as desired to provide specific properties to the overall material and/or to provide specific properties to coatings of the polymer composition as applied to a substrate (e.g., a specific article of manufacture, such as a glove or condom).

The hydrogel-forming component utilized in the present compositions can be any suitable, water-soluble polymer that, when applied as a coating layer on a substrate, is adapted to or configured to form a hydrogel. In some embodiments, the water-soluble polymer can be a material that is adapted to or configured to form an interpenetrating polymer network. More particularly, the water-soluble polymer can be adapted to or configured to form an interpenetrating polymer network with the latex component of the polymer composition. For example, in some embodiments, the water-soluble polymer may be adapted to or configured to form a gel due a least in part to hydrogen bonding between long, linear chains of the polymer and other associations between the polymer chains. Likewise, chains of the latex polymer component may extend into neighboring particles. Further, one or both polymer materials may become entrapped within the interpenetrating network of the other component and form linkages therebetween. As such, in some embodiments, it can be particularly useful for the water-soluble polymer to include long, linear chains that are configured for arranging into interpenetrating polymer networks that can readily form hydrogels via hydrogen bonding. In further embodiments, the water-soluble polymer particularly may be a homopolymer. Moreover, it can be useful in some embodiments for the water-soluble polymer to include a low incidence of crosslinks between the groups on the polymer that participate in crosslinking. For example, in some embodiments, less than 10%, less than 5%, less than 2%, or less than 1% of the crosslinkable groups of the water-soluble polymer will be crosslinked. In further embodiments, the water-soluble polymer may be substantially non-crosslinked, indicating that only an insignificant of the crosslinkable groups of the water-soluble polymer are actually crosslinked, such insignificant content being 5% or less, 2% or less, 1% or less, 0.5% or less, or 0.1% or less.

In some embodiments, polyethylene oxides (PEO) can be particularly useful as a water-soluble polymer according to the present disclosure. Polyethylene oxides may be available in a wide range of materials exhibiting a scale of useful properties. In some embodiments, it can be beneficial to utilize a PEO having, for example, a molecular weight within a defined range. In some embodiments, the PEO preferably has a molecular weight of at least 1,000,000 Da, at least 2,000,000 Da, or at least 3,000,000 Da. For example, a maximum molecular weight may be up to about 10,000,000 Da. In some embodiments, the molecular weight may be about 2,000,000 Da to about 6,000,000 Da, about 2,500,000 Da to about 5,500,000 Da, about 3,000,000 Da to about 5,000,000 Da, or about 3,500,000 Da to about 4,500,000 Da.

Molecular mass can be expressed as a weight average molecular mass ($M_w$) or a number average molecular mass ($M_n$). Both expressions are based upon the characterization of macromolecular solute containing solution as having an average number of molecules ($n_i$) and a molar mass for each molecule ($M_i$). Accordingly, number average molecular mass is defined by formula 1 below.

$$M_n = \frac{\sum n_i M_i}{\sum n_i} \quad (1)$$

Weight average molecular mass (also known as molecular mass average) is directly measurable using light scattering methods and is defined by formula 2 below.

$$M_w = \frac{\sum n_i M_i^2}{\sum n_i M_i} \quad (2)$$

Molecular mass can also be expressed as a Z-average molar mass ($M_z$), wherein the calculation places greater emphasis on molecules with large molar masses. Z-average molar mass is defined by formula 3 below.

$$M_z = \frac{\sum n_i M_i^3}{\sum n_i M_i^2} \quad (3)$$

Unless otherwise noted, molecular mass is expressed herein as weight average molecular mass and is thus referenced as a molecular weight.

In addition to molecular mass, polymer solutions can also be physically described in terms of polydispersity, which represents the broadness of the molecular mass distribution within the solution, such distribution being the range of different molecular masses of the individual polymer molecules in the solution. Polydispersity is the ratio of the number average molecular mass to the weight average molecular mass, which is defined by formula 4 below.

$$\text{Polydispersity} = \frac{M_w}{M_n} \quad (4)$$

If polydispersity is equal to 1 (i.e., $M_n$ equals $M_w$), the polymer is said to be monodisperse. A truly monodisperse polymer is one where all polymer molecules within the solution are of a single, identical molecular mass. As $M_n$ changes with $M_w$, the polydispersity changes, always being greater than 1. The polydispersity of a given polymer solution can affect the physical characteristics of the polymer, and, therefore, the interaction of the polymer with another polymer. In some embodiments, the PEO used according to the present invention has a polydispersity close to 1. In example embodiments, the PEO can have a polydispersity of 1 to about 4, about 1 to about 3, or about 1.1 to about 2.5. Such values can likewise be applicable to other water-soluble polymers used according to the present disclosure. Maintaining a polydispersity value that is substantially close to 1 can be beneficial since significant changes from a desired molecular weight range can adversely affect material properties as described herein. For example, unacceptably low molecular weights can negatively affect the desired sensory properties of the coating layer that is applied to the underlying article.

Although PEO polymers may be particularly useful as a water-soluble polymer according to the present disclosure, other types of water-soluble polymers may also be utilized, particularly when further components of the present hydrogel-latex composition are included to provide a stabilizing effect, as further described below. In particular, any water-soluble polymer that is adapted to or configured to form a hydrogel and is also stable in combination with the latex polymer may be utilized. PEO, for example, is a non-ionic polymer, and similar non-ionic polymers may likewise be utilized. As non-limiting examples, in some embodiments, one or more of the following water-soluble polymers may also be utilized: hyaluronic acids and salt forms thereof (e.g., sodium hyaluronate); cellulosic polymers; derivatives of cellulosic polymers (e.g., carboxymethylcellulose, hydroxyethylcellulose, hydroxy methylcellulose, and similar derivatives); polysaccharides, such as alginic acids and derivatives thereof (e.g., alginates). In further embodiments, water based polyurethanes and/or crosslinked polyacrylic acid polymers may be utilized. For example, an anionic (polyurethane/acrylate) copolymer blend may be used. Anionic polymers in particular (e.g., alginates, cellulose derivatives, such as carboxymethylcellulose, and hyaluronates) may be utilized. While anionic polymers can be preferred, in some embodiments, polymers including cationic groups may likewise be utilized if the system includes sufficient negatively charged moieties to reduce the charge density of an otherwise cationic polymer. For example, polyampholytes may be utilized in some embodiments. Polyampholytes are understood to reference polymeric systems including monomeric components of varying charge. Suitable polyampholytes may include polymer systems wherein at least 10%, at least 25%, or at least 50% by weight of the monomer units forming the polymer are anionic (e.g., about 10% to about 95%, about 25% to about 90%, or about 50% to about 90% anionic monomers), said percentages being wt/wt, based on the total weight of the polymer. Although the above examples are listed individually, it is understood that a blend of water-soluble polymers likewise may be used. Such blends may be utilized in a variety of ratios. For example, a first water-soluble polymer and a second-water soluble polymer (e.g., any two polymers listed above) may be used in a ratio of 1:5 to 5:1, 1:4 to 4:1, 1:3 to 3:1, 1:2 to 2:1, or about a 1:1 ratio (wt/wt). In some embodiments, certain types of water-soluble polymers may be excluded. For example, cationic polymers may be excluded as such polymers have been found to lead to phase separation when compounded with rubber latex materials. In particular embodiments, when useful, any specific polymer listed herein may be expressly excluded.

The water-soluble polymer(s) used to prepare the polymer compositions described herein preferably can be utilized as an aqueous solution. As such, the actual polymer(s) will particularly be prepared as an aqueous solution such that the aqueous solution comprises the polymer material solubilized in water at a concentration such that the aqueous solution has a suitable viscosity for further processing as described herein and/or at a concentration that is below the solubility limit for the particular polymer used. In example embodiments, water soluble polymers for use herein can solubilized at a concentration of about 0.1% to about 5%, about 0.25% to about 4%, about 0.5% to about 3%, or about 1% to about 3% by weight of the polymer based on the total weight of the aqueous solution. The solubilized polymer may be referenced as a hydrogel. This hydrogel thus may be modified through addition of one or more further components as further discussed below. The modified hydrogel combined with the latex component discussed herein may then be referenced as the hydrogel-latex composition.

In some embodiments, the water-soluble polymer(s) may be the predominant component of the polymer compositions, meaning that the weight percentage of the water-soluble polymer(s) present in the composition (as an aqueous polymer solution) is greater than the weight percentage of any other individual component of the composition. In some embodiments, the water-soluble polymer (or combination of polymers) may be present in the polymer compositions in an amount of up to about 60% by weight, based on the total weight of the polymer composition (i.e., the hydrogel-latex composition). In some embodiments, the water-soluble polymer can be present in an amount of under 50% by weight based on the total weight of the hydrogel-latex composition. Still further, the water-soluble polymer may be present in a minimum content of at least 10% by weight, at least 15% by weight, at least 20% by weight, at least 30% by weight, or at least 40% by weight (e.g., up to a maximum of about 75%) based on the total weight of the composition. In particular embodiments, the water-soluble polymer can be present in the total composition (as an aqueous solution) in an amount of about 15% to about 60% by weight, about 20% to about 58% by weight, about 22% to about 55% by weight, or about 24% to about 50% by weight based on the total weight of the composition.

The latex component utilized in the present compositions can be any latex material that is combinable with the water-soluble polymer (e.g., will form a stable mixture and thus will not separate into discrete partitions). In one or more embodiments, one or both of a natural rubber latex ("NRL") and a synthetic rubber latex polymer may be utilized. Non-limiting examples of synthetic rubber latex polymers that may be used include synthetic polyisoprene, synthetic poly(styrene-isoprene-styrene) ("SIS"), intermediate modulus ("IM") styrene ethylene butylene styrene ("SEBS"), high modulus ("HM") SEBS, water-based polyurethane, nitrile rubber (e.g., acrylonitrile butadiene rubber, or "NBR"), styrene-co-butadiene, styrene-co-isoprene, triblock copolymers, such as styrene-block-butadiene and block styrene (SBS), and similar, synthetic latex polymers in the form of homopolymers and/or co-polymers. In some embodiments, NRL can be particularly useful for combination with the water-soluble polymer component. Further, in some embodiments, a synthetic rubber latex polymer may be expressly excluded from the present compositions. Likewise, if desired (e.g., as an option to minimize or eliminate any reaction by individuals exhibiting an allergy to NRL), a natural rubber latex may be expressly excluded from the present compositions. The latex component can be particularly useful for providing elastomeric properties to the polymer composition and/or for improving bonding between the polymer composition and any substrate, product, article, or the like to which the polymer composition may be applied as a coating, as further described herein.

In some embodiments, the latex component utilized in the present compositions may be at least partially pre-vulcanized. As such, the latex particles may be characterized as including intra-particle crosslinks. Likewise, some level of inter-particle crosslinking may be present.

In some embodiments, the latex component can be present in the polymer composition in an amount that can be substantially equal to or less than the amount of the water-soluble polymer that is present. For example, the latex component (e.g., one or both of a natural or synthetic rubber latex) can be present in total amount (e.g., all of any one or more latex components that are present) of less than 30% by weight based on the total weight of the hydrogel-latex composition. In some embodiments, the latex component can be present in a minimum amount of at least 5%, at least 10%, or at least 15% by weight (e.g., up to a maximum of 45% by weight in embodiments wherein the water-soluble polymer is the predominant component of the composition), based on the total weight of the composition. More particularly, the latex component can be present in an amount of about 10% to about 30% by weight, about 15% to about 30%, or about 20% to about 25% by weight, based on the total weight of the composition. The latex component can be utilized in the polymer composition as an aqueous dispersion, and the foregoing ranges can relate to the amount of the aqueous dispersion that is included in the polymer composition. The aqueous dispersion can have a solids content of about 5% to about 65%, about 10% to about 55%, or about 20% to about 50%. In some embodiments, a low solids content can be utilized, such as about 5% to about 30%, about 5% to about 25%, or about 10% to about 20%. In other embodiments, a high solids content can be utilized, such as about 30% to about 65%, about 40% to about 65%, or about 45% to about 60%. In any case, the amount of the aqueous dispersion of the latex component can be adjusted within the ranges noted above so that the total solids content of the hydrogel-latex composition is within the ranges otherwise noted herein.

The latex component of the present compositions may be utilized in a substantially unmodified state (i.e., comprising substantially only the latex polymer itself and any water used to form the aqueous dispersion of the latex polymer). In other embodiments, however, it can be useful to utilize a latex component in a compounded form (i.e., combined with one or more further materials), which may be indicative of the latex being at least partially prevulcanized and/or postvulcanized, as noted above. For example, the aqueous dispersion of the latex polymer may include one or both of a crosslinking agent and a cure accelerator. In some embodiments, it may be preferred for any accelerator utilized in the latex component to be substantially or completely free of zinc. For example, sodium N-dialkyl dithiocarbamates and dithiocarbamate blends may be utilized as accelerators. Suitable vulcanizing agents that may be utilized in some embodiments can include diisopropyl xanthogen polysulfide, sulfur (e.g., free sulfur, such as being present in an $S_8$ configuration), and sulfur donors. Suitable accelerating agents (i.e., accelerators) that may be utilized can include dithiocarbomates, thiaxoles, and xanthates, with particular, non-limiting examples including TMTD, TETD, ZDEC, and ZDBC. Suitable sulfur donors can include one or more thiurams, such as dipentamethylenethiuram hexasulfide (DPTTH), dipentamethylenethiuram tetrasulfide (DPTT), tetramethylthiuram monosulfide (TMTM), tetramethylthiuram disulfide (TMTD), tetraethylthiuram disulfide (TETD), and tetrabenzylthiuram disulfide (TBzTD). Additionally, or alternatively, other types of sulfur donors may also be utilized. For example, 4,4'-dithiodimorpholine (DTDM), thiocarbamyl sulfonamide, and N-oxydiethylene thiocarbamyl-N-oxydiethylene sulfenamide (OTOS) may be utilized in some embodiments. Suitable antioxidants that may be utilized in some embodiments can include amine derivatives or phenolic derivatives (e.g., diphenyl-p-phenylenediamine, 1,2-dihydro-2,2,4-trimethylquinoline, poly (dicyclopentadiene-co-p-cresol). Suitable surfactants that may be utilized in some embodiments can include anionic surfactants, cationic surfactants, or amphoteric surfactants (e.g., sodium lauryl sulfate, sodium polynaphthalene sulfonate, sodium polymethacrylate, and potassium laurate). Suitable fillers that may be used in some embodiments can include one or both of inorganic and organic fillers (e.g., fumed silica and zinc oxide). Further, in some embodiments, a cure activator, such as zinc oxide, may be used.

In some embodiments, it can be particularly useful to include one or more rheological stabilizers in the polymer composition. Such components may be beneficial to impart stability to the polymer blend by, for example, reducing or prevent phase separation in the completed composition, particularly when the composition is present as a coating layer on an article. Likewise, the presence of one or more rheological stabilizers can be effective to improve pick-up of the hydrogel-polymer composition on the surface of the article to which it is applied. Improved "pick-up" can mean imparting greater uniformity of the ultimate coating layer, thus avoiding thin spots or even voids in the coating layer. Preferably, polymer compositions according to the present disclosure, either being stable in the express exclusion of any rheological stabilizer, or being stable when a rheological stabilizer is expressly included, exhibit a stability such that the polymer composition alone or the polymer composition when present as a coating layer on an article does not separate into visibly identifiable, separate layers for at least a defined time. In some embodiments, sufficient stability may be characterized in relation to a minimum degree of visibly identifiable phase separation. For example, a stable composition or layer thereof may be defined in relation to exhibiting less than 10%, less than 5%, less than 2%, less than 1%, or exhibiting 0% phase separation for a time of at least one week, at least two weeks, at least one month, at least 2 months, or at least six months when stored at ambient conditions.

A rheological stabilizer can be a component that may be adapted to or configured to provide or increase thixotropy of the polymer composition. The polymer composition thus can be thixotropic in nature and may exhibit improved coating uniformity when applied to a substrate. The separate water-soluble, hydrogel-forming component and the latex component can separately exhibit properties that provide a desirable, combined material. For example, the water soluble, hydrogel-forming component can be adapted to or configured to be shear thinning between 3 rpm to 100 rpm such that greater than 65%, greater than 70%, greater than 75%, or greater 80% of the original viscosity is lost under shear, while the latex component can be adapted or configured such that less than 65%, less than 60%, or less than 55% of its original viscosity is lost over the same rpm range as measured on a Brookfield viscometer LV. The overall polymer composition may be adapted to or configured to exhibit a dynamic yield in the range of about 40 dyne-cm to about 125 dyne-cm, about 50 dyne-cm to about 120 dyne-cm, or about 60 dyne-cm to about 115 dyne-cm. The ability to provide the hydrogel-polymer composition in a liquid form that is shear thinning form and with a yield value as noted above is beneficial in that it improves the ability to coat the hydrogel-polymer composition onto a surface of a latex article in a manner with the coating will be maintained on the surface of the article during curing, without dripping or other loss of the composition.

In one or more embodiments, useful rheological stabilizers can be any additive, particularly a polymer additive, that is adapted to or configured to improve film uniformity and/or stability without significantly adversely affecting other film properties. Particularly useful rheological stabilizers can include one or more materials categorized as a hydrophobically modified alkali swellable emulsion ("HASE") polymer. Known HASE materials that may be utilized according to the present disclosure include materials which preferably include structural units of a) an acrylate, for example ethyl acrylate, butyl acrylate, or ethylhexyl acrylate, preferably ethyl acrylate; b) an acid, preferably acrylic acid, methacrylic acid, itaconic acid, or phosphoethyl methacrylate, preferably acrylic acid or methacrylic acid; and c) an alkylated ethoxylate monomer, preferably an alkylated ethoxylate acrylate or methacrylate. In some embodiments, useful HASE polymers include materials comprising ethyl acrylate, methacrylic acid, and hydrophobically modified (e.g., with $C_{22}$ behenyl pendant groups) methacrylate with 25 moles of ethoxylation. In a non-limiting example embodiment, a suitable HASE material is available under the name Novethix™ L-10 and is an acrylates/beheneth-25 methacrylate copolymer. In one or more embodiments, a single HASE material or a total HASE material content in a polymer composition according to the present disclosure can be in an amount of less than 1% by weight based on the total weight of the composition. In further embodiments, the rheological stabilizer can be present in an amount of at least 0.01%, at least 0.05%, or at least 0.1% by weight based on the total weight of the polymer composition. More particularly, the rheological stabilizer can be present in an amount of about 0.01% to about 3% by weight, about 0.01% to about 1% by weight, about 0.05% to about 0.8% by weight, about 0.1% to about 0.6% by weight, about 0.15% to about 0.5%, or about 0.2% to about 0.4% by weight, based on the total weight of the polymer composition.

In some embodiments, the polymer composition in its final form (e.g., as the hydrogel-latex composition), ready for coating onto an article, may be adapted to or configured to exhibit a defined viscosity, which may be inclusive or exclusive of any rheological stabilizer component. For example, the polymer composition prior to being applied to a substrate may exhibit a viscosity of about 300 cP to about 2,200 cP, about 500 cP to about 1,2,100 cP, about 700 cP to about 2,000 cP, or about 800 cP to about 1,900 cP.

The polymer composition, in one or more embodiments, may be provided with a specific total solids content. This may be adjusted accordingly, such as by reducing or increasing the specific weight percentage of total polymer components present in the composition. More particularly, this may be controlled through increasing or reducing the water content of the polymer composition. In particular, the water-soluble polymer and the latex polymer component can be present in a sufficient amount such that the polymer composition has a total solids content of about 2.0% to about 20%, about 3% to about 18%, about 4% to about 16%, about 5% to about 15%, about 6% to about 13%, about 7% to about 12%, or about 8% to about 10%.

Water may be provided in the polymer composition in a sufficient content to provide the proper dilution and total solids content. Preferably, water is included in an amount sufficient to achieve a 100% composition total after accounting for the polymer components, any rheological stabilizer, and any further components that may be included in the polymer composition.

In some embodiments, it may be useful to expressly exclude one or more materials from a polymer composition as present disclosed. For example, any one or more of antimicrobials, antifungals, antibiotics, vitamins, and the like may be expressly excluded from a polymer composition according to one or more embodiments of the present disclosure. If desired, however, one or more of such items may be included.

In an example embodiment, a polymer composition (i.e., a hydrogel-latex composition) according to the present disclosure may include the following: about 20% to about 48% by weight of a water-soluble polymer (e.g., as an aqueous polymer solution); about 15% to about 30% by weight of a natural or synthetic rubber latex (e.g., as an aqueous dispersion of the natural or synthetic rubber latex); about 0.01% to about 0.5% by weight of a rheological stabilizer; and the balance water; wherein the foregoing amounts are based on the total weight of the hydrogel-latex composition. In some embodiments, the above composition of natural or synthetic rubber latex, rheological stabilizer, and water may further include a surfactant in an amount of about 0.01% to about 5%, to about 4%, to about 3%, to about 2%, or to about 1% by weight based on the total weight of the hydrogel-latex composition. In some embodiments, the above composition of natural or synthetic rubber latex, rheological stabilizer, and water may further include a filler in an amount of about 0.01% to about 3%, to about 2%, to about 1%, or to about 0.5% by weight based on the total weight of the hydrogel-latex composition. In some embodiments, the above composition of natural or synthetic rubber latex, rheological stabilizer, and water may further include an accelerator in an amount of about 0.01% to about 2%, to about 1%, to about 0.5%, or to about 0.1% by weight based on the total weight of the hydrogel-latex composition. In some embodiments, the above composition of natural or synthetic rubber latex, rheological stabilizer, and water may further include a sulfur donor in an amount of about 0.01% to about 2%, to about 1%, to about 0.5%, or to about 0.1% by weight based on the total weight of the hydrogel-latex composition. It is specifically understood, however, that any of the foregoing amounts may be appropriately adjusted to encompass any of the further weight ranges for the noted components as otherwise disclosed herein.

In one or more embodiments, the present disclosure encompasses a variety of products that may have one or more surfaces that are at least partially coated with a polymer composition as described herein. The polymer compositions are suitable for coating of any article, particularly polymeric articles, where it may be desirable to provide at least a portion of an article surface with a lubricious property. This may extend to a wide variety of products, including devices, implants, and other articles suitable for use in the medical field. In particular embodiments, the polymer compositions are suitable for coating surfaces of elastomeric articles. As such, a product with a coating according to the present disclosure may be a product that comprises an elastomeric latex. Such product may be formed substantially entirely from the elastomeric latex or may have only a portion thereof formed from the elastomeric latex. In such products, at least a portion of the elastomeric latex can be coated with a polymer composition (i.e., a hydrogel-latex composition) according to any of the embodiments described herein.

In one or more embodiments, the present disclosure particularly can encompass an article that includes a latex layer defining the article and a layer of a polymer composition as described herein present on at least a portion of the latex layer (e.g., coated on at least a portion of an outer surface and/or coated on at least a portion of an inner surface of the latex layer). The latex article may be specifically an elastomeric latex article. A wide variety of latex articles may be coated with a polymer composition as described herein. The coated latex articles may be formed sequentially such that the latex article is first made and then sent directly to a coating process wherein the polymer composition is coated onto the latex article. In other embodiments, the polymer composition described herein may be applied to a commercially available, pre-formed latex article. In some embodiments, the latex article (i.e., an article formed of a layer of a latex composition) may particularly define a condom. In other embodiments, the latex article may particularly define a glove. The latex article may be formed of a layer of a natural rubber latex, may be formed of a layer of a synthetic polymer latex, or may be formed of a layer of a combination of a natural rubber latex and a synthetic polymer latex. For example, any one or more of natural rubber latex, polyisoprene, SIS polymer, butadiene, styrene-butadiene, nitrile, isobutylene, and the like may be utilized as the primary component of the latex article. Coating of the hydrogel-polymer composition onto the latex article may be by any suitable method, such as spraying, rolling, dipping, or the like.

In some embodiments, the layer of the polymer composition as described herein may be provided with a specific layer thickness. For example, the polymer composition may be provided with an average thickness of about 10 µm to about 100 µm, about 12 µm to about 75 µm, or about 15 µm to about 50 µm. Since many latex articles, particularly elastomeric latex articles, such as gloves and condoms, are specifically configured to have a very small thickness, it can be preferable for the layer thickness of the polymer composition applied to the latex article to be less than the average thickness of the latex article to which it is applied. For example, the thickness of the polymer composition layer may be about 95% or less, about 90% or less, about 75% or less, about 50% or less, about 40% or less, or about 35% or less of the average thickness of the latex article. More particularly, the average thickness of the polymer composition layer may be about 2% to about 90%, about 5% to about 75%, or about 10% to about 50% of the average thickness of the polymer composition layer. If desired, the average thickness of the layer of the polymer composition may be greater than the average thickness of the latex article. For example, the average thickness of the polymer composition layer may be at least 5%, at least 10%, at least 25%, at least 50%, at least 75%, or at least 100% greater than the average thickness of the latex article to which it is applied. A "layer" of the hydrogel-polymer composition as used above references the total content of the hydrogel-polymer composition as applied as a single coating or as a plurality of coatings that cure, dry, or process to the final form the overall layer.

The polymer composition may be added to a substrate, such as a latex article, via a variety of suitable mechanisms. For example, the polymer composition may be substantially adhered to the underlying article. In embodiments wherein the polymer composition is layered onto a latex article, the inclusion of the latex component in the polymer composition may be effective to enhance adhesion of the water-soluble polymer to the underlying latex surface through at least chemical bonding. While not wishing to be bound by theory, in some embodiments, the water-soluble, hydrogel-forming polymer may be at least partially entrapped within at least a portion of the latex component during coalescence and cohesion of the individual latex particles. Additionally, the water-soluble polymer component may be further locked into the polymer matrix due to polymer chain interdiffusion during the process. In some embodiments, the combination of the hydrogel-polymer composition layer with the latex article can be particularly defined in relation to the express absence of any independent adhesives, glues, or similar chemical compounds or compositions that may be available for adhering together of relatively thin layers.

The presence of the layer of the polymer composition of the present disclosure on at least a portion of a surface of the latex article can be beneficial to impart a variety of desirable properties to the latex article. For example, the presence of the polymer composition as a layer on at least a portion of the latex article can significantly improve wettability of the latex article. Improved wettability can provide for more rapid transfer of liquid across a surface and therefor can have a direct impact on the ability to improve lubricity. A layer of a polymer composition of the present disclosure can exhibit a lower contact angle in relation to a fluid deposited thereon as compared to the underlying latex article itself. For example, a layer of a latex composition defining the underlying article (when uncoated) can exhibit a first contact angle, and a layer of the present polymer composition provided on at least a portion of the latex article can exhibit a second contact angle that is less than the first contact angle. More particularly, the second contact angle (i.e., the contact angle exhibited by a surface of a layer of a polymer composition of the present disclosure) can be less than the first contact angle (i.e., the contact angle exhibited by the surface of the latex article when uncoated) by at least 5 degrees, at least 7 degrees, at least 8 degrees, or at least 10 degrees. In some embodiments, a contact angle exhibited by a surface of a layer of a polymer composition as described herein can be about 30 degrees or less, about 28 degrees or less, about 25 degrees or less, or about 23 degrees or less (e.g., with a lower range approaching zero).

A coated article according to the present disclosure, particularly in light of the presence of the coating layer of the polymer composition described above, may specifically be adapted to or configured to reduce frictional forces that may arise when the coated article is in contact with other surfaces, and particularly when in contact with human tissue.

In one or more embodiments, the present disclosure may further provide one or more methods of preparing a polymer composition and/or a coated article. In some embodiments, a hydrogel-latex polymer composition may be prepared by separately forming a solution of the water-soluble polymer and a dispersion of the latex component and then combining the water-soluble polymer solution into the latex dispersion. The further components may be added separately to the individual solution or dispersion or may be added to the combined formulation.

The presently disclosed hydrogel-polymer compositions beneficially can provide improved sensory properties to a variety of underlying articles, include elastomeric latex articles, such as gloves and condoms. Moreover, such added characteristics have substantially no deleterious effect on further properties of the articles. For example, elastomeric latex articles are desired to exhibit high strength (e.g., high tensile modulus) and good stretch properties. It has been shown through testing that the application of a hydrogel-polymer coating does not negatively affect the desired physical characteristics of the underlying article. Likewise, the formed coating layers have been found to remain substantially undisturbed (e.g., exhibiting little flaking and substantially no delamination) even under repeated cycles of extension (e.g., up to 500% elongation) of elastomeric articles with the hydrogel-polymer composition applied thereto. The hydrogel-polymer compositions thus beneficially form a coating layer on the underlying articles that can be dried or otherwise cured to form a substantially powdery feeling layer on the article, the layer being effective for re-hydration upon contact with aqueous fluids (e.g., water and bodily fluids) as well as synthetic lubricants to thus achieve a hydrated, slippery coating layer that is effective for imparting good lubricity to the article.

EXPERIMENTAL

The present disclosure is more fully illustrated by the following examples, which are set forth to illustrate certain embodiments of the present disclosure and are not to be construed as limiting thereof.

Example 1—Preparation of Hydrogel Latex Composition (Pre-Vulcanized Latex)

Two formulations were prepared. An aqueous solution of a PEO polymer (Polyox™, available from DuPont) was prepared at a concentration of 2% by weight by mixing at approximately 150 rpm to 200 rpm until hydrated and uniform. For the latex component, 1) compounded latex having a solid content of approximately 52% was produced, and 2) an aqueous pre-vulcanized latex composition having a solid content of 61% was obtained from Centrotrade and diluted to approximately 50% solids. The PEO solution was weighed into the compounded latex mixing at 150 rpm to form Formulation 1, and the PEO solution was weighed into the pre-vulcanized latex mixing at 150 rpm to form Formulation 2. Novethix L-10 was diluted with the remaining amount of deionized water and weighted into the compositions with continued mixing at 150 rpm for approximately 15 minutes. The compositions were diluted to a final solids content of 6.0%-13.0%. The compounded latex was filtered using cheese cloth and then transferred to a dip tank overnight to remove air bubbles. The formulations are shown in Table 1 below. The compounded NRL was formed of NRL (available as Centex HF) at 100 phr, casein (0.05 phr), ammonium hydroxide (0.007 phr), Darvan® #1 (0.10 phr), Sulfur dispersion (1.50 phr), zinc oxide dispersion (0.82 phr), Setsit® #5 (0.210 phr), Butyl Namate (0.090 phr), and Wingstay® L (0.50 phr). The prevulcanized latex was purchased from MMG under the tradename PVH 7/001.

TABLE 1

Hydrogel Blend Formulation

| | | Formulations (wt/wt %) | |
|---|---|---|---|
| Ingredient | Function | 1 | 2 |
| Polyethylene oxide (2% solution) | Hydrogel-former | 48% | 48% |
| Novethix ™ L-10 (30% solids) | Thickener/Stabilizer | 0.33% | 0.33% |
| Compounded NRL (48-52% solids) | Elastomeric material | 22.25% | 0 |
| Prevulcanized Latex (60-61% solids) | Elastomeric material | 0 | 18.96% |
| QS water | Dilution | 29.42% | 32.71% |

Example 2—Preparation of Latex Articles

Latex articles were prepared utilizing the formulations prepared according to Example 1. The latex articles were prepared by performing three dipping actions. The first and second dip in the dip tank was carried out at a withdrawal speed of about 0.1 to 0.4 inches per second to obtain the desired film thickness and oven dried at about 104° C. for about 4 minutes. A third dip in the hydrogel-latex blend dip tank was carried out at a withdrawal speed of about 0.1 to 0.6 inches per second to obtain the desired film thickness and oven dried at about 132° C. for about 10 minutes. The formed elastomeric latex article was removed from the former using a 0.5% ammonia leach solution then a corn starch slurry and oven dried.

Example 3—Property Testing

A hydrogel-blend coated condom (dipped three times) was compared to a compounded latex condom that did not include a hydrogel-blend coating. The condoms were tested on a Texture Analyzer equipped with a 40 mm small sled. The equipment contains a platform having a friction sled attached to a load cell which is constrained to slide across the platform over which a lubricant is applied. Load is provided by a 300 g weight positioned centrally over the sled. This arrangement was used to measure the coefficient of sliding friction over a fixed period of time. The Plexiglas™ sled was covered with the compounded latex condom or the hydrogel-blend coated condom, and a 4.0 mil film of water based Magnum Premium Lubricant was cast onto the liner. The study generated a coefficient of friction data for an extended period of approximately fifteen (15) minutes which was translated to lubricity as in Equation (5), where is the coefficient of friction, $F_f$ is the force of friction, $F_n$ is the normal force, and lubricity is the reciprocal of the coefficient of friction. The graph of the test results is shown in FIG. 1.

$$\mu = F_f/F_N; \text{Lubricity} = \mu^{-1} \quad (5)$$

The lubricity was found to be lower under the initial conditions used for the lubricity testing. The hydrogel-blend coated condom was found to be very hydrophilic and continuously absorb moisture in the film during the 15 minutes of testing. Lubricity is interpreted as being the inverse of the coefficient of friction ($\mu$). The more drag that is experienced on the surface, the lower the measured lubricity. As such, higher lubricity values are seen as evidence of improved properties according to the present disclosure. Testing illustrated in FIG. 1 indicated that the film became pliable and pulled under the movement of the sled, which indicated that additional soak time was needed to fully hydrate and activate the film coating. The improved values achieved with proper hydration of the film coating are discussed below and in relation to FIG. 3.

The hydrophilicity of the hydrogel-blend coated film was further verified by examination of the contact angle and water absorption testing. A latex film was prepared by hand dipping a glass slide with two coatings of compounded latex then drying five minutes at approximately 104° C. between each coating. A hydrogel-blend film was prepared by hand dipping a glass slide with two coatings of compounded latex then drying at approximately 104° C. between each coating followed by a third dip of hydrogel-blend. The contact angle was then measured by the sessile drop technique and image analysis to generate a tangent at the intersections of the drop outline. This generated a baseline contact angle for the latex-only coating of 33.5 degrees and a baseline contact angle of the hydrogel-polymer coating of 21 degrees. The drop used to contact each film was deionized water for both film surfaces, and the evaluation was carried out at 3 different locations on each slide to provide an average contact angle values noted above. The hydrogel-blend coated latex was found to have a significantly lower contact angle and less spherical shape to the drop placed on the film.

Figure 2:
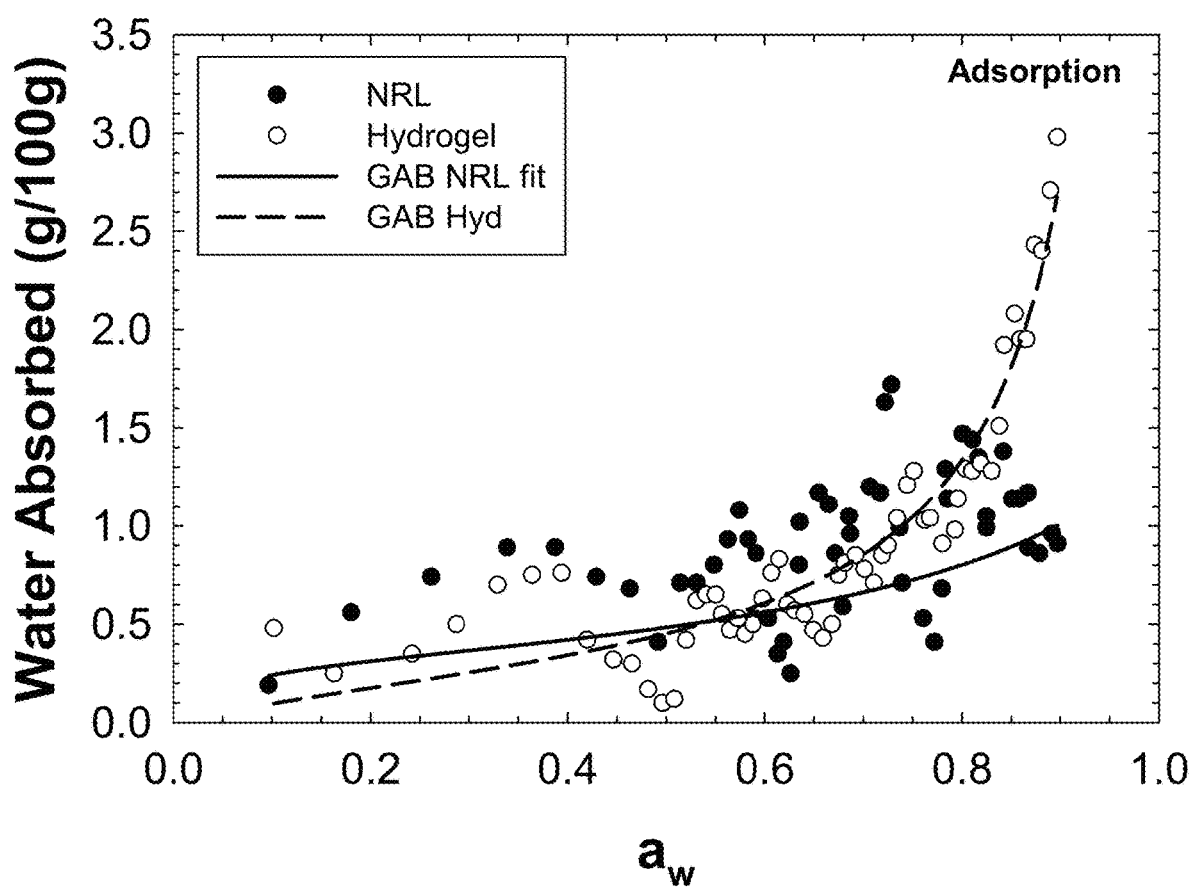
FIG. 2 is a graph showing vapor sorption analysis a varying relative humidity of a compounded latex condom versus a latex condom coated with a hydrogel-blend composition according to embodiments of the present disclosure.

Compounded latex condoms and hydrogel-blend condoms prepared as discussed above were evaluated for moisture adsorption and retention using a vapor sorption analyzer (VSA). The VSA passed humidified air over a 100 g film taken from the compounded latex condom and 100 g film taken from the hydrogel-blend condom (from Example 1 above) and measured both the weight and water activity. The plots that were obtained show adsorption curves for compounded latex and hydrogel-blend condoms. Moisture uptake, in g water per 100 g of condom material are plotted against water activity, which can be viewed as relative humidity ($a_w = 1$ corresponds to 100% RH). The lines represent fits of a common adsorption model (DLP model). The Hydrogel-blend condom adsorbed significantly more moisture at the high water activity (i.e. greater than about aw=0.85). The results are shown in FIG. 2.

Example 4—16 Hour Soaking Lubricity Testing

The lubricity of the 3 dip hydrogel-blend coated condom from Example 1 was compared again to a 2 dip compounded latex condom. The condoms were tested on a Texture Analyzer equipped with a 40 mm small sled such that the coefficient of friction was calculated according to ASTM D1894. The equipment contains a platform having a friction sled attached to a load cell which is constrained to slide across the platform over which a lubricant is applied. Load is provided by a 300 g weight positioned centrally over the sled. This arrangement was used to measure the coefficient of sliding friction over a fixed period of time after the lubricant soak period. The Plexiglas™ sled was covered with the one compounded latex condom and one hydrogel-blend coated condom respectively. The condom covered Plexiglas™ sled was allowed to soak in a petri dish filled with approximately 40 g of the water based Magnum™ Premium Lubricant overnight for approximately 16 hours. After the 16-hour time period was reached, a 4.0 mil film of water based Magnum™ Premium Lubricant was cast onto the liner and the test was run. The study generated a coefficient of friction data for an extended period of approximately fifteen (15) minutes which was translated to lubricity as in Equation (5). The results are shown in the graph provided in FIG. 3.

The lubricity was found to be significantly higher for the hydrogel-blend condom after extended period of lubricant absorption into the film prior to conducting the lubricity testing particularly in the first 200 seconds. The hydrogel-blend coated condom was found to be very hydrophilic and more pliable during 15 minutes of testing.

Example 5—Surface Morphology

The addition of the hydrogel-blend coating was found to create a unique morphology on the condom surface that is not flat but provides a significant number of peaks and valleys, which can reduce the contact surface with skin of the user. Internal laboratory panelists described the dry sensory as smoother and powdery in feel. Since only protruding portions of the coating (i.e., the "peaks") are in contact with the skin of the user this may improve dry feel and possibly wet sensory. The pores in the film appear to aid in the moisture absorption properties and possibly allow lubricant to be released from the film at a later point as the lubricity was greatly improved after 16 hr of soaking. The surface morphology of the hydrogel-polymer coated sample and the uncoated sample is seen in FIG. 4A and FIG. 4B, respectively. The hydrophilic nature of the film coupled with the porous topography may provide for the unique sensory benefit as noted herein and may provide for release of lubricant at a later point from the film during use.

Example 6—Hydrogel Polymer Stability Evaluations

Multiple hydrogel-polymer compositions were prepared utilizing various types of water soluble polymers and then evaluated for shelf stability, dry sensory properties, and wet sensory properties. The results of such testing are provided below in Table 2 through Table 4.

TABLE 2

| | | Formulations (wt/wt %) | | | |
|---|---|---|---|---|---|
| Ingredient | Function | 3 | 4 | 5 | 6 |
| PEO (2% solution) | Hydrogel | 37.5% | 48% | 48% | 0 |
| PEO (1.55% solution) | Hydrogel | 0 | 0 | 0 | 48% |
| Novethix™ L-10 (30% solids) | Thickener/Stabilizer | 0 | 0.33% | 0.33% | 0.25% |

TABLE 2-continued

| Ingredient | Function | Formulations (wt/wt %) | | | |
|---|---|---|---|---|---|
| | | 3 | 4 | 5 | 6 |
| Compounded NRL (48-52% solids) | Elastomeric material | 0 | 22.25% | 0 | 0 |
| Prevulcanized Latex (60-61% solids) | Elastomeric material | 19.5% | 0 | 18.96% | 13.41% |
| QS water | Dilution | 43% | 29.42% | 32.71% | 38.34% |
| 1 Week Shelf Stability | | Phase Separated | Stable 2 months | Stable 2 months | Stable 2 months |
| Dry Sensory | | Powdery | Powdery | Powdery | Powdery |
| Wet Sensory | | Very slippery | Very slippery | Very slippery | Very slippery |

TABLE 3

| Ingredient | Function | Formulations (wt/wt %) | | |
|---|---|---|---|---|
| | | 6 | 7 | 8 |
| Carboxymethylcellulose (2% solution) | Hydrogel | 25% | 0 | 0 |
| Hydroxypropyl methylcellulose (Methocel E4M) | Hydrogel | 0 | 48% | 0 |
| Hydroxypropyl methylcellulose (Methocel ™ J75MS-N) | Hydrogel | 0 | 0 | 48% |
| Novethix™ L-10 (30% solids) | Thickener/Stabilizer | 0 | 0.25% | 0.25% |
| Prevulcanized Latex (60-61% solids) | Elastomeric material | 19.5% | 13.41% | 13.41% |
| QS water | Dilution | 55.50% | 38.34% | 38.34% |
| 1 Week Shelf Stability | | Gel bodies present | Stable | Stable |
| Dry Sensory | | Rough | Powdery | Powdery |
| Wet Sensory | | Textured and slightly slippery | Slippery | Slippery |

TABLE 4

| Ingredient | Function | Formulations (wt/wt %) | | | |
|---|---|---|---|---|---|
| | | 9 | 10 | 11 | 12 |
| Alginate (Hydagen 558P) | Hydrogel | 48% | 0 | 0 | 0 |
| Sodium Hyaluronate (2% solution) | Hydrogel | 0 | 37.5% | 0 | 0 |
| N-Hance ™ 3000 (guar hydroxypropyl trimonium) | Hydrogel | 0 | 0 | 48% | 0 |
| Jaguar ® C162 (guar hydroxypropyl trimonium chloride) | Hydrogel | 0 | 0 | 0 | 48% |
| Novethix ™ L-10 (30% solids) | Thickener/Stabilizer | 0.25% | 0 | 0.25% | 0.25% |
| Prevulcanized Latex (60-61% solids) | Elastomeric material | 13.41% | 18.96% | 13.41% | 13.41% |
| QS water | Dilution | 38.34% | 43.54% | 38.34% | 38.34% |
| 1 Week Shelf Stability | | Stable | Stable | Immediate separation | Immediate separation |
| Dry Sensory | | Powdery | Powdery | Powdery | Powdery |
| Wet Sensory | | Slipper | Not slippery | NA | NA |

Example 7—Alternative Method of Preparation of Hydrogel-Latex Compositions Using Pre-Vulcanized Latex Into a vessel, deionized water was added in a weight amount necessary to achieve a final dilution of solids content between 6.0%-13.0%. Novethix™ L-10 was next added to the vessel with mixing at 100 rpm for approximately 5 minutes. An aqueous 1.55% solution of PEO (see Example 1) was prepared as a side phase by mixing with high agitation for incorporation, and mixing was then reduced to approximately 150 rpm to 200 rpm for remaining mixing until fully hydrated and uniform. The PEO side phase was then weighed into the latex mixing at 150 rpm. An aqueous pre-vulcanized latex composition having a solid content of 61% was obtained from Centrotrade and added with mixing. The pre-vulcanized latex included zinc oxide, zinc bis (dibutyldithiocarbamate) and NRL. The compounded latex was filtered using cheese cloth and then transferred to a dip tank overnight to remove air bubbles.

Example 8—Preparation of Latex Articles

Latex articles were prepared utilizing the composition prepared according to Example 1 or Example 7. The latex articles were prepared by performing three dipping actions. The first and second dip in the dip tank was carried out at a withdrawal speed of about 0.1 to 0.4 inches per second to obtain the desired film thickness and oven dried at about 115° C. for about 1.3 minutes. A third dip in the hydrogel-latex blend dip tank was carried out at a withdrawal speed of about 0.1 to 0.6 inches per second to obtain the desired film thickness and oven dried at about 132° C. for about 4 minutes. The formed elastomeric latex article was removed from the former using a 0.4% sodium hydroxide solution then a corn starch slurry and oven dried.

Example 9—Adhesion and Strength Testing

Testing samples were prepared as described in Example 8. A "3-dip" article was prepared to include a single coating layer of the hydrogel-latex composition over the cured latex condom (formed with two dippings). A "2-dip" article was prepared as a comparative—i.e., including the latex condom (formed with two dippings) without the hydrogel-latex coating. The 3-dip coated condom and the 2-dip condom without the coating were tested on a Texture Analyzer TA.XT2 Texture Analyzer with 5 kg load cell and equipped with a modified TA-227 test rig, from Texture Technologies. The Test rig TA-227 was modified to have 3 mm round pins. This arrangement was used to stretch 10 mm films of the hydrogel-blend coated condom compared with 10 mm films of the 2 dip latex condom films. The 3-dip condom with the hydrogel-latex coating and the 2-dip condom were cut into 10 mm strips with tested 10 mm strip and non-tested 10 mm strip for visual inspection. To test the degree of adhesion of the coating on the substrate, a stretch test was performed after the coating had cured on the condom by stretching and pulling the film from its rest position to a position that is 100% 200%, 300%, 400% and 500% stretched, and the stretched sample was then released back to its rest position. A hold time of 60 seconds was used for the stretched position, and a relax time of 30 seconds was used between stretchings. Once the coated film has been stretched, the coating of the film was examined visually to see if the coating had delaminated or flaked off.

The coating adhesion test showed that the hydrogel-latex coating layer did not visually delaminate or flake off of the substrate in a substantial amount after being stretched. The stretched and non-stretched films had similar appearance with no change in the film appearance until 400% elongation and 500% elongation which had slight flaking observed with no obvious delamination of the film.

Ring tensile testing was conducted per ASTM-D3492 for comparison of the hydrogel-latex coated condom and non-coated latex condom using dippings as follows: the latex composition was applied with two dippings where the former was removed at speeds of about 0.2 in/sec to about 0.3 in/sec to form the base layer; the hydrogel-latex composition was applied to the base layers using a dipping removal speed of about 0.2 in/sec to about 0.3 in/sec to form the top coat. Tensile testing of the hydrogel-latex coated condoms revealed similar results compared with the latex control base layer indicating that the hydrogel-latex coating did not weaken the latex material (tensile modulus of 15.7 for the uncoated condom and 20.6 for the coated condom). Dimensional analysis data per ASTM D3492-16 indicated the condoms to be comparable in length, width, and thickness to commercially available condoms.

Use of the words "about" and "substantially" herein are understood to mean that values that are listed as "about" a certain value or "substantially" a certain value may vary by an industry recognized tolerance level for the specified value. When an industry recognized tolerance is unavailable, it is understood that such terminology may indicate that an acceptable value may be vary ±3%, ±2%, or ±1% from the specifically listed value. More particularly, where a temperature is disclosed, "about" or "substantially" may indicate the specifically listed temperature ±2° C., ±1° C., or ±0.5° C. Likewise, in some embodiments, the listed value may be exact, if desired, and variations above or below the listed value may be expressly excluded.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A hydrogel-latex composition comprising:
   a water-soluble polymer present as an aqueous solution in an amount of under 50% by weight based on the total weight of the hydrogel-latex composition;
   a natural or synthetic rubber latex; and
   a rheological stabilizer;
   wherein the water-soluble polymer and the natural or synthetic rubber latex are present in a sufficient amount such that the hydrogel-latex composition has a total solids content of about 2.0% to about 20%.

2. The hydrogel-latex composition of claim 1, wherein the water-soluble polymer is configured to form an interpenetrating polymer network.

3. The hydrogel-latex composition of claim 1, wherein the water-soluble polymer has a molecular weight of about 1,000,000 to about 6,000,000.

4. The hydrogel-latex composition of claim 1, wherein the water-soluble polymer is a polyethylene oxide.

5. The hydrogel-latex composition of claim 1, wherein the natural or synthetic rubber latex is compounded with one or both of a crosslinking agent and a cure accelerator.

6. The hydrogel-latex composition of claim 1, wherein the natural or synthetic rubber latex is at least partially pre-vulcanized.

7. The hydrogel-latex composition of claim 1, wherein the rheological stabilizer is a hydrophobically modified alkali swellable emulsion ("HASE") polymer.

8. The hydrogel-latex composition of claim 1, wherein the water-soluble polymer is present as an aqueous solution in an amount of about 15% to about 48% by weight based on the total weight of the hydrogel-latex composition.

9. The hydrogel-latex composition of claim 1, wherein the natural or synthetic rubber latex is present as an aqueous dispersion in an amount of 30% or less by weight based on the total weight of the hydrogel-latex composition.

10. The hydrogel-latex composition of claim 9, wherein the natural or synthetic rubber latex is present as an aqueous dispersion in an amount of about 10% to about 30% by weight based on the total weight of the hydrogel-latex composition.

11. The hydrogel-latex composition of claim 1, wherein the rheological stabilizer is present in an amount of less than 1% by weight based on the total weight of the hydrogel-latex composition.

12. The hydrogel-latex composition of claim 11, wherein the rheological stabilizer is present in an amount of about 0.01% to about 0.25% by weight based on the total weight of the hydrogel-latex composition.

13. The hydrogel-latex composition of claim 1, wherein the water-soluble polymer is a homopolymer.

14. The hydrogel-latex composition of claim 1, wherein the water-soluble polymer is substantially non-crosslinked.

15. The hydrogel-latex composition of claim 1, comprising:

about 20% to about 48% by weight of an aqueous solution of the water-soluble polymer;

about 15% to about 30% by weight of an aqueous dispersion of the natural or synthetic rubber latex;

about 0.01% to about 0.5% by weight of the rheological stabilizer; and balance water;

wherein the foregoing amounts are based on the total weight of the hydrogel-latex composition.

16. A product comprising an elastomeric latex with at least a portion of the elastomeric latex being coated with the hydrogel-latex composition of claim 1.

17. An elastomeric article comprising:

a layer of a latex composition; and a layer of a hydrogel-latex composition according to claim 1 present on at least a portion of the layer of the latex composition.

18. The elastomeric article of claim 17, wherein the layer of the latex composition defines a condom.

19. The elastomeric article of claim 17, wherein the layer of the latex composition comprises a natural rubber latex.

20. The elastomeric article of claim 17, wherein the layer of the latex composition comprises a synthetic polymer latex.

21. The elastomeric article of claim 17, wherein a layer of the latex composition that does not have a layer of the hydrogel-latex composition present thereon exhibits a first contact angle, and wherein the layer of the hydrogel-latex composition present on at least a portion of the layer of the latex composition exhibits a second contact angle that is less than the first contact angle.

22. The elastomeric article of claim 21, wherein the second contact angle is less than the first contact angle by at least 5 degrees.

23. The elastomeric article of claim 17, wherein the layer of the hydrogel-latex composition has a thickness of about 10 μm to about 100 μm.

24. An elastomeric article prepared by a process comprising:

coating at least a portion of an article defined by at least one layer of a latex composition with at least one layer of a hydrogel-latex composition according to claim 1; and drying the article.

25. The elastomeric article of claim 24, wherein the article defined by at least one layer of a latex composition is a condom.

26. The elastomeric article of claim 24, wherein the latex composition comprises a natural rubber latex.

27. The elastomeric article of claim 24, wherein the latex composition comprises a synthetic polymer latex.

* * * * *